United States Patent
Collazo

(10) Patent No.: US 8,192,441 B2
(45) Date of Patent: Jun. 5, 2012

(54) HIGH TIBIAL OSTEOTOMY INSTRUMENTATION

(75) Inventor: Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 904 days.

(21) Appl. No.: 12/287,061

(22) Filed: Oct. 3, 2008

(65) Prior Publication Data

US 2010/0087824 A1    Apr. 8, 2010

(51) Int. Cl.
*A61F 5/00* (2006.01)
(52) U.S. Cl. .................... 606/87; 606/86 R; 606/88
(58) Field of Classification Search ............. 606/87, 606/86 R, 88
See application file for complete search history.

(56) References Cited

U.S. PATENT DOCUMENTS

| | | | |
|---|---|---|---|
| 4,409,973 A | 10/1983 | Neufeld | |
| 4,421,112 A | 12/1983 | Mains et al. | |
| 4,456,006 A | 6/1984 | Wevers et al. | |
| 4,509,511 A | 4/1985 | Neufeld | |
| 4,565,191 A | 1/1986 | Slocum | |
| 4,608,898 A | 9/1986 | Volk | |
| 4,627,425 A | 12/1986 | Reese | |
| 4,632,102 A | 12/1986 | Comparetto | |
| 4,677,973 A | 7/1987 | Slocum | |
| 4,750,481 A | 6/1988 | Reese | |
| 4,852,558 A | 8/1989 | Outerbridge et al. | |
| 4,913,144 A | 4/1990 | Del Medico et al. | |
| 5,041,117 A | 8/1991 | Engelhardt | |
| 5,053,039 A | 10/1991 | Hofmann et al. | |
| 5,304,180 A | 4/1994 | Slocum | |
| 5,540,695 A | 7/1996 | Levy | |
| 5,601,565 A | 2/1997 | Huebner | |
| 5,613,969 A | 3/1997 | Jenkins, Jr. | |
| 5,620,448 A | 4/1997 | Puddu et al. | |
| 5,722,978 A | 3/1998 | Jenkins, Jr. | |
| 5,749,875 A | 5/1998 | Puddu et al. | |
| 5,766,251 A | 6/1998 | Koshino et al. | |
| 5,897,559 A | 4/1999 | Masini | |
| 5,911,724 A * | 6/1999 | Wehrli ............................ 606/88 |
| 5,980,526 A | 11/1999 | Johnson et al. | |
| 6,008,433 A | 12/1999 | Stone | |
| 6,059,787 A | 5/2000 | Allen | |
| 6,086,493 A | 7/2000 | Goshima et al. | |
| 6,086,593 A | 7/2000 | Bonutti | |
| 6,203,546 B1 | 3/2001 | MacMahon | |
| 6,348,054 B1 | 2/2002 | Allen | |
| 6,423,061 B1 | 7/2002 | Bryant | |
| 6,544,266 B1 | 4/2003 | Roger et al. | |
| 6,575,982 B1 | 6/2003 | Bonutti | |
| 6,823,871 B2 | 11/2004 | Schmieding | |

(Continued)

OTHER PUBLICATIONS

U.S. Appl. No. 11/480,648.

(Continued)

*Primary Examiner* — Andrew Yang
(74) *Attorney, Agent, or Firm* — Lerner, David, Littenberg, Krumholz & Mentlik, LLP

(57) ABSTRACT

An apparatus to aid in cutting a bone during a bone osteotomy procedure, including a frame having a first bushing, a first fixation pin, and an adjustment screw. The apparatus further includes a side plate attached to the frame and moveable with respect thereto, the side plate having a second bushing and a second fixation pin. In addition, the apparatus includes a drill block assembly releasably attached to the side plate and moveable with respect thereto, the drill block having a third bushing and a hinge pin.

23 Claims, 10 Drawing Sheets

U.S. PATENT DOCUMENTS

| | | |
|---|---|---|
| 2002/0164905 A1 | 11/2002 | Bryant |
| 2002/0165552 A1 | 11/2002 | Duffner |
| 2002/0198451 A1 | 12/2002 | Carson |
| 2003/0105526 A1 | 6/2003 | Bryant et al. |
| 2003/0171757 A1 | 9/2003 | Coon et al. |
| 2003/0195516 A1 | 10/2003 | Sterett et al. |
| 2003/0228288 A1 | 12/2003 | Scarborough et al. |
| 2005/0075641 A1 | 4/2005 | Singhatat et al. |
| 2005/0154394 A1 | 7/2005 | Michalowicz |
| 2005/0251147 A1 | 11/2005 | Novak |
| 2005/0273112 A1 | 12/2005 | McNamara |
| 2005/0273114 A1 | 12/2005 | Novak |
| 2006/0122617 A1 | 6/2006 | Lavallee et al. |
| 2006/0217808 A1 | 9/2006 | Novak et al. |
| 2006/0241636 A1 | 10/2006 | Novak et al. |
| 2007/0016209 A1 | 1/2007 | Ammann et al. |
| 2007/0213830 A1 | 9/2007 | Ammann et al. |
| 2007/0244487 A1 | 10/2007 | Ammann et al. |
| 2008/0015603 A1 | 1/2008 | Collazo |
| 2008/0015604 A1 | 1/2008 | Collazo |
| 2008/0015605 A1 | 1/2008 | Collazo |
| 2008/0140213 A1 | 6/2008 | Ammann et al. |
| 2008/0147073 A1 | 6/2008 | Ammann et al. |
| 2008/0147074 A1 | 6/2008 | Ammann et al. |
| 2008/0154267 A1 | 6/2008 | Merchant et al. |
| 2008/0167654 A1 | 7/2008 | Novak et al. |
| 2008/0208197 A1 | 8/2008 | Ammann et al. |
| 2008/0208199 A1 | 8/2008 | Ammann et al. |
| 2008/0243257 A1 | 10/2008 | Taber |
| 2009/0018543 A1 | 1/2009 | Ammann et al. |
| 2009/0043308 A1 | 2/2009 | Horacek |
| 2009/0054899 A1 | 2/2009 | Ammann et al. |
| 2009/0076512 A1 | 3/2009 | Ammann et al. |

OTHER PUBLICATIONS

U.S. Appl. No. 11/478,790.
U.S. Appl. No. 11/478,788.
Outerbridge et al., Stryker Howmedica Osteonics Surgical Techniques, High Tibial Osteotomy Using FirstStep Implants and Instruments.
International Search Report, PCT/US2007/014977, dated May 7, 2008.
CD Newton, Principles and Techniques of Osteotomy, Jan. 1, 1985, IVIS, CH. 40.
Henderson et al., Adolescent tibia vara: alternatives for operative treatment, 1992, JBJS-Am, 74, 342-350.
DK Pal et al., Blount's disease in a patient of Indian lineage—A case report, Apr. 2003, IJO, 37-2.
WB Greene, Infantile tibia vara, 1993, JBJS-Am, 75, 130-143.
Office Action from U.S. Appl. No. 11/478,790, mailed Jun. 10, 2009.

\* cited by examiner

HIGH TIBIAL OSTEOTOMY INSTRUMENTATION

BACKGROUND OF THE INVENTION

High tibial osteotomy ("HTO") procedures have become well-established means of treating unicompartmental degenerative arthritis of the knee. This condition occurs due to uneven weight bearing of the femoral condyles on either of the medial or lateral joint compartments of the tibia. Such uneven weight bearing results from either a varus or valgus defect in the tibia. A varus or valgus defect occurs when the knee joint shifts either medially (valgus) or laterally (varus) with respect to the mechanical axis. It is generally accepted that the preferred location for the mechanical axis of the knee is at about 62% of the tibial plateau from medial to lateral. The process for determining the location of the mechanical axis is known in the art. A varus deformity generally results in increased loading on the medial joint compartment, while a valgus defect results in increased loading on the lateral joint compartment. A high-tibial osteotomy procedure uses one of various techniques to bring the knee into proper mechanical alignment by correcting a deformity therein, whether varus or valgus.

One existing high-tibial osteotomy procedure is the opening wedge HTO. In this procedure, a single cut is made from, for example, the medial cortex of the tibia across to near the lateral cortex in order to correct a varus defect. The cut in an opening wedge HTO procedure extends through almost the entire tibia, leaving only enough bone on the lateral tibia to form a hinge section which serves to keep the tibial plateau connected to the remainder of the bone. The cut is then forced open to form a wedge having an angle corresponding to the required amount of angular correction. This procedure can also be used to correct a valgus defect, with the cut originating on the lateral tibia, extending through the tibia to near the medial tibia. The necessary cut is typically made using a cutting guide, of which various forms are known, affixed to the tibia.

Upon completion of the cut, the cutting guide, should one be used in the procedure, is removed and the bone is typically displaced by inserting two plates into the cut and turning a jackscrew. A metal wedge may also be used to expand the wedge cut by impacting the wedge into the cut and advancing it until the desired amount of correction is achieved. Once the cut is opened, an appropriately shaped spacer can be inserted into the cut to support the tibial plateau at the desired angle. The spacer can be made of a known bone-substitute material, an autograft taken from the patient's iliac crest or an allograft taken from a donor. The wedge is then secured in place using hardware typically in the form of bone plates and screws.

An alternative procedure is what is known as a closing-wedge osteotomy. In such a procedure, a wedge of bone is removed from the tibia, closing the opening left by the removal of the wedge, and securing the bone in its new configuration. The wedge is shaped to correspond to the appropriate amount of angular correction necessary to bring the knee joint into proper alignment. Generally the wedge is shaped so as to span almost the entire medial-lateral width of the tibia, leaving only a narrow "hinge" section of bone on the closed end of the wedge. Once the bone wedge is resected, the opening is forced closed and is typically held in such a position using a staple or other similar device, including bone screws and/or plates. Such procedures are shown in U.S. Pat. No. 5,980,526 to Johnson, et al.; U.S. Pat. No. 6,796,986 to Duffner; U.S. Pat. No. 5,911,724 to Wehrli; U.S. Pat. No. 5,053,039 to Hoffman, et al.; U.S. Pat. No. 5,540,695 to Levy, and; U.S. Pat. No. 5,601,565 to Huebner.

Various tools have been developed in order to facilitate both the opening and closing wedge osteotomy procedures. Typically, these tools include various cutting guides which are capable of being affixed to the bone and provide a surface which is used to guide a bone saw or other known instrument into proper alignment for the desired cut or cuts. Examples of such guides are shown in commonly owned U.S. patent application Ser. Nos. 11/478,788, 11/478,790, 11/480,648, and 11/788,377, the disclosures of which are incorporated herein by reference. Typically, these guides are designed to affix to either the medial or lateral side of the tibia, depending on the type of correction required and the procedure used. By taking either a medial or lateral approach for cutting, the patellar tendon is easily avoided. However, these approaches make alignment of cuts more difficult because the mechanical axis is not visible from the side of the knee. It is difficult to position a cutting guide relative to the tibia to ensure that the cut made in the above procedure is aligned correctly. Accordingly, there is a need in the art for instrumentation to assist in positioning the cutting guide during performance of an HTO.

SUMMARY OF THE INVENTION

The present invention relates to an apparatus to aid in cutting a bone during a bone osteotomy procedure. The apparatus may include a frame having a first bushing, a first fixation pin, an adjustment screw, and a side plate attached to the frame and moveable with respect thereto. The side plate may have a second bushing and a second fixation pin. The apparatus may further include a drill block releasably attached to the side plate and moveable with respect thereto, the drill block having a third bushing and a hinge pin.

In a preferred embodiment, the first bushing may be oriented adjacent, and the first fixation pin may be configured to penetrate, the medial cortex of the tibia. The first fixation pin may be configured to penetrate a tibia at a location about one to two centimeters below a knee joint.

Furthermore, the second bushing may be oriented adjacent, and the second fixation pin may be configured to penetrate, the lateral cortex of a tibia. The first and second fixation pins may be configured to penetrate a tibia at an orientation parallel to the joint line and the coronal plane thereof. Furthermore, the second fixation pin may be configured to penetrate a tibia at a location about one to two centimeters below a knee joint.

The adjustment screw of the frame may also be configured to contact the anterior tibia and adjust the angle of the frame with respect to the anatomic anterior-posterior slope of the tibia. The hinge pin may be configured to fully penetrate the posterior-lateral cortex of a tibia. Furthermore, the longitudinal axis of the third bushing may be offset a predetermined distance from the tip of the second bushing, thereby ensuring that a desired minimum lateral cortex bone thickness remains.

A further embodiment of the present invention relates to a method of cutting a bone during a bone osteotomy procedure. The method may include providing an alignment device having a first bone referencing portion, a second bone referencing portion, and a third bone referencing portion, with the third bone referencing portion having a hinge pin guide. The method may further include securing the first bone referencing portion to the medial cortex of a tibia and securing the second bone referencing portion to the lateral cortex of the tibia. The third bone referencing portion may be positioned adjacent the anterior-lateral cortex of the tibia with the hinge pin guide parallel to the anatomic anterior-posterior slope of the tibia by rotating the device about the first and second referencing portions. In a preferred embodiment, the method may further include inserting a hinge pin into the tibia through the hinge pin guide, attaching a cutting guide to the hinge pin, and forming a cut using a cutting instrument in connection with the cutting guide.

In a further embodiment of the method, the alignment device may include a frame and the first bone referencing portion may include a first bushing engaged with the frame. Furthermore, the method may include the step of providing a first fixation pin forming a part of the first bone referencing portion and configured to secure the first bone referencing portion to the tibia at a position between about one to two centimeters below a knee joint.

An alternative embodiment of the method may further include orienting the first fixation pin parallel to the joint line and the coronal plane of the tibia. Furthermore, the method may include providing a side plate configured to engage with the frame and a second bushing engaged with the side plate and forming a part of the second bone referencing portion. The method may also include offsetting the longitudinal axis of the hinge pin guide a predetermined distance from the tip of the second bushing, thereby ensuring that a desired minimum lateral cortex bone thickness remains.

In a preferred embodiment, the method may further include the step of providing a second fixation pin forming a part of the second bone referencing portion and configured to secure the second bone referencing portion to the tibia at a position between about one to two centimeters below a knee joint. The method may further include orienting the second fixation pin parallel to the joint line and the coronal plane of the tibia and providing an adjustment screw attached to the frame. The adjustment screw may be configured to contact the anterior tibia and determine the orientation of the frame with respect to the anatomic anterior-posterior slope of the tibia.

An alternative embodiment of the present invention relates to a method of cutting a bone during a bone osteotomy procedure. The method includes the step of providing an alignment frame having a side plate and a drill block. The frame may have an adjustment screw and be configured to receive a first bushing. The side plate may be moveable with respect to the frame and configured to receive a second bushing. The drill block may be releasably attached and moveable with respect to the side plate and configured to receive a third bushing.

A preferred embodiment of the method may include placing the first bushing against the medial cortex of a tibia and inserting a first pin through the first bushing and into the tibia. The method may further include moving the side plate along the frame in a medial direction and attaching the second bushing thereto such that the second bushing contacts the lateral cortex of the tibia, and inserting a second pin through the second bushing and into the tibia. Furthermore, the method may include advancing the adjustment screw until it contacts the anterior tibia and the drill block is oriented parallel to the anatomic anterior-posterior slope of the tibia, and inserting a hinge pin through the third bushing and into the anterior-lateral cortex of the tibia. The hinge pin may be inserted through the third bushing and into the anterior-lateral cortex of the tibia, the cutting guide may be attached to the hinge pin, and a cut may be formed through a portion of the tibia using a cutting instrument in connection with cutting guide surfaces of the cutting guide.

In a preferred embodiment, the method may further include inserting the first pin into the tibia at a location about one to two centimeters below a knee joint, inserting the second pin into the tibia at a location about one to two centimeters below a knee joint, and coaxially aligning the first and second pins parallel to the joint line and the coronal plane of the tibia.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

BRIEF DESCRIPTION OF THE DRAWINGS

The present invention will be better understood on reading the following detailed description of nonlimiting embodiments thereof, and on examining the accompanying drawings, in which.

DETAILED DESCRIPTION

In describing preferred embodiments of the alignment apparatus of the present invention, reference will be made to directional nomenclature used in describing the human body. It is noted that this nomenclature is used only for convenience and that it is not intended to be limiting with respect to the scope or structure of the invention. When referring to specific directions, the device is understood to be described only with respect to its orientation and position during an exemplary application to the human body.

Figure 1:
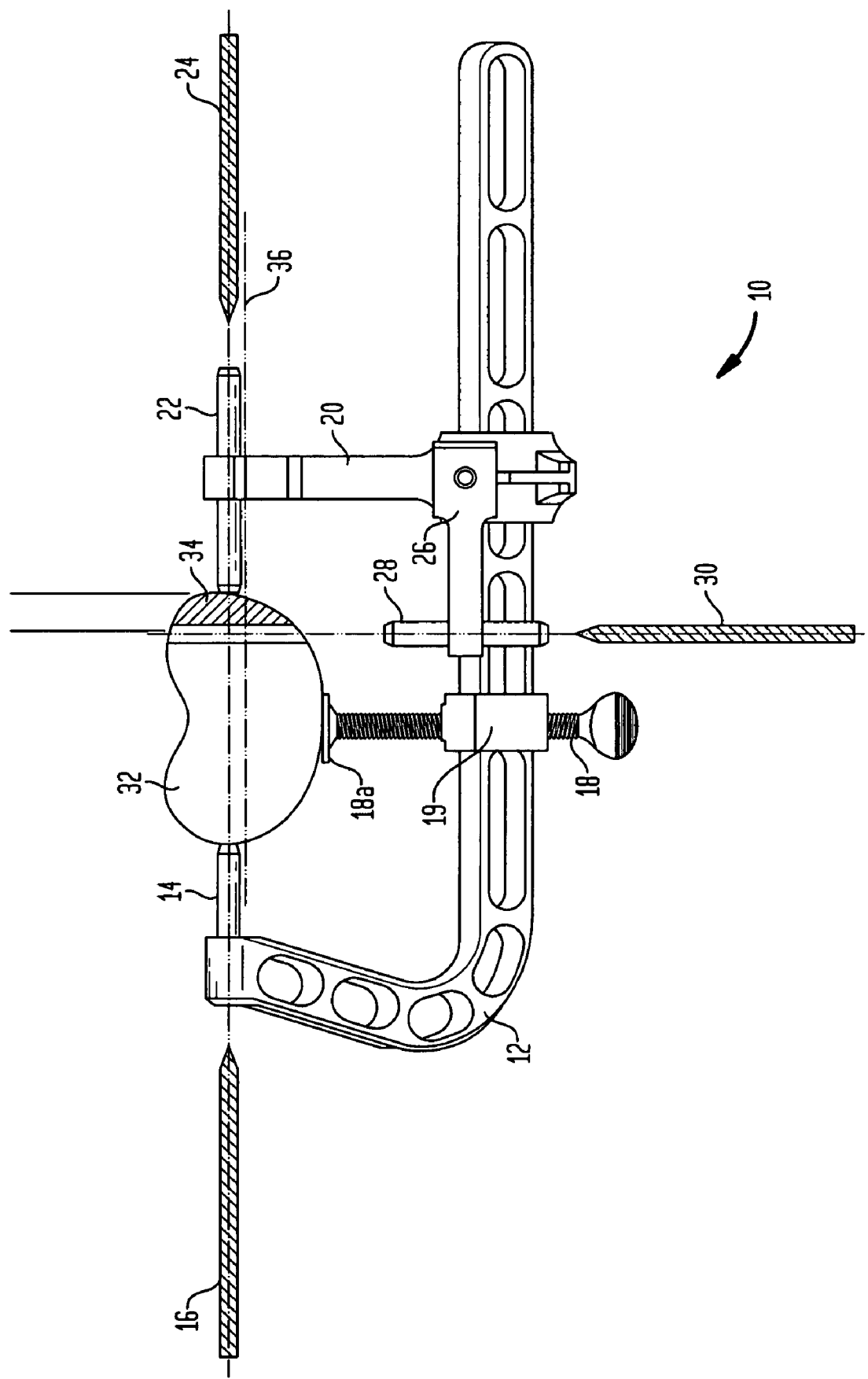
FIG. 1 is a top view of an alignment apparatus according to an embodiment of the present invention.
Figure 2:
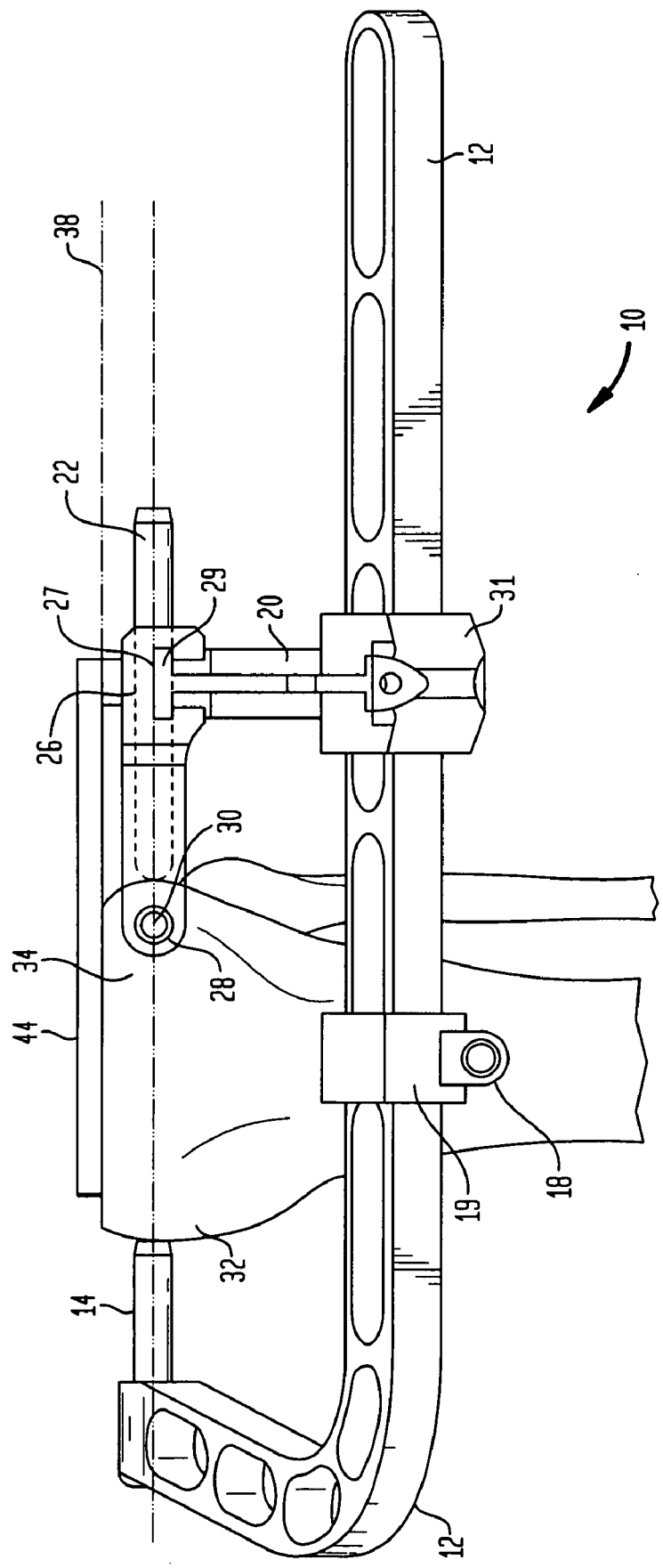
FIG. 2 is an anterior elevation view of the alignment apparatus shown in FIG. 1.

Referring now to the drawings wherein like reference numerals indicate similar features, FIGS. 1 and 2 show an exemplary embodiment of an alignment apparatus 10 to aid in positioning a cutting guide during an HTO procedure according to an embodiment of the present technology. Generally, alignment device 10 is adapted to be affixed to a bone surface, and, in the particular embodiment shown in FIGS. 1 and 2, is adapted to be affixed to a human tibia so as to align a cutting guide on the anterior surface of the proximal portion of the human tibia. Alignment apparatus 10 includes a frame 12, a side plate 20, and a drill block 26.

Frame 12 includes a first drill guide bushing 14 configured to be placed against the medial cortex 32 of a tibia. A first fixation pin 16, guided by first bushing 14, is inserted through first bushing 14 and into the bone at a position approximately one to two centimeters below the joint line 38. Side plate 20, which is moveable with respect to frame 12, includes a second drill guide bushing 22 configured to be placed against the lateral cortex 34 of the tibia. A second fixation pin 24, guided by the second bushing 22, is inserted through the second bushing 22 and into the bone at a position approximately one to two centimeters below the joint line 38. Alignment apparatus 10 is properly configured when the longitudinal axes of fixation pins one and two are parallel to both the joint line 38 and the coronal plane 36. A fixation pin slope indicator 44 may assist in referencing the orientation of the longitudinal axes of the first and second fixation pins relative to the joint line 38 and the coronal plane 36. In one embodiment, the surgeon may align fixation pin slope indicator 44 with the joint line 38 and coronal plane 36 using fluoroscopic visualization. Because side plate 20 is moveable with respect to frame 12, alignment apparatus 10 can be adjusted to fit the particular anatomy of the patient.

Drill block 26 includes a third drill guide bushing 28 configured to be placed against the anterior-lateral cortex of the tibia. Drill block 26 is attached to side plate 20 and is moveable in the anterior-posterior direction relative thereto. At the point of attachment, drill block 26 is configured to define a recess 27 having a shape suitable to engage a protrusion 29 (shown in FIG. 4) extending outwardly from side plate 20. Protrusion 29 is configured to correspond to recess 27 such that side plate 20 and drill block 26 are fixedly engaged in the lateral and vertical directions, but free to move relative to each other in the anterior-posterior direction.

A flexion/extension adjustment screw 18 is attached to frame 12 and has a bone contact disc 18a which rests on the anterior tibia. Adjustment screw 18 may be attached to frame 12 by means of a securing member 19 defining a threaded hole 17 through which adjustment screw 18 passes. Securing member 19 is configured to fix the position of screw 18 in a vertical as well as anterior-posterior direction relative to frame 12. Preferably, securing member 19 allows movement of screw 18 in a lateral direction, although such movement may be restricted by means of a set screw (not shown) or friction fit. Screw 18 may be advanced or retracted with respect to threaded hole 17, thereby adjusting the position of securing member 19 and frame 12 relative to the bone. When the desired position of screw 18 in hole 17 is achieved, screw 18 may be fixed relative to hole 17 by means of frictional forces between the threads of the screw and the hole.

Accordingly, the configuration of the adjustment screw 18 with respect to third bushing 28 is such that as adjustment screw 18 advances or retracts, frame 12 pivots about pins 16 and 24 so that the angle of the longitudinal axis of the third bushing 28 relative to the anatomic anterior-posterior slope of the tibia 40 (shown in FIG. 3) changes. The alignment apparatus 10 is properly configured when the adjustment screw 18 is advanced to the point that the longitudinal axis of the third bushing 28 is parallel to the anatomic anterior-posterior slope of the tibia 40. A hinge pin slope indicator 42 (shown in FIGS. 3 and 4) may assist in referencing the anatomic anterior-posterior slope of the tibia 40. In one embodiment, the surgeon may align the hinge pin slope indicator 42 with the anatomic anterior-posterior slope of the tibia 40 using fluoroscopic visualization. A hinge pin 30, guided by third bushing 28, is inserted through the anterior-lateral cortex of the tibia with the longitudinal axis of hinge pin 30 parallel to the anatomic anterior-posterior slope of the tibia 40. The longitudinal axis of the third bushing 28 is offset from the tip of the second bushing 22 to ensure that a minimum lateral cortex bone thickness remains after the hinge pin 30 penetrates the bone.

Figure 3:
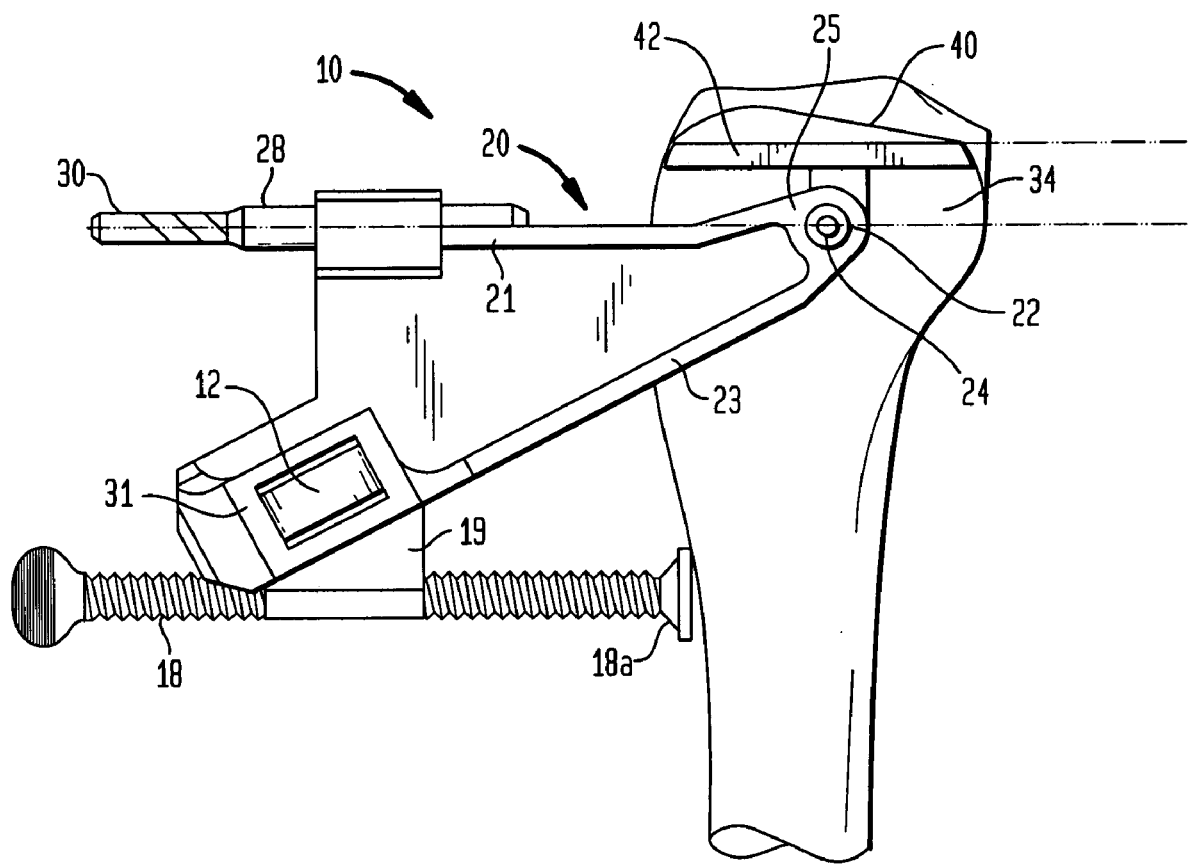
FIG. 3 is a lateral elevation view of the alignment apparatus shown in FIG. 1.
Figure 4:
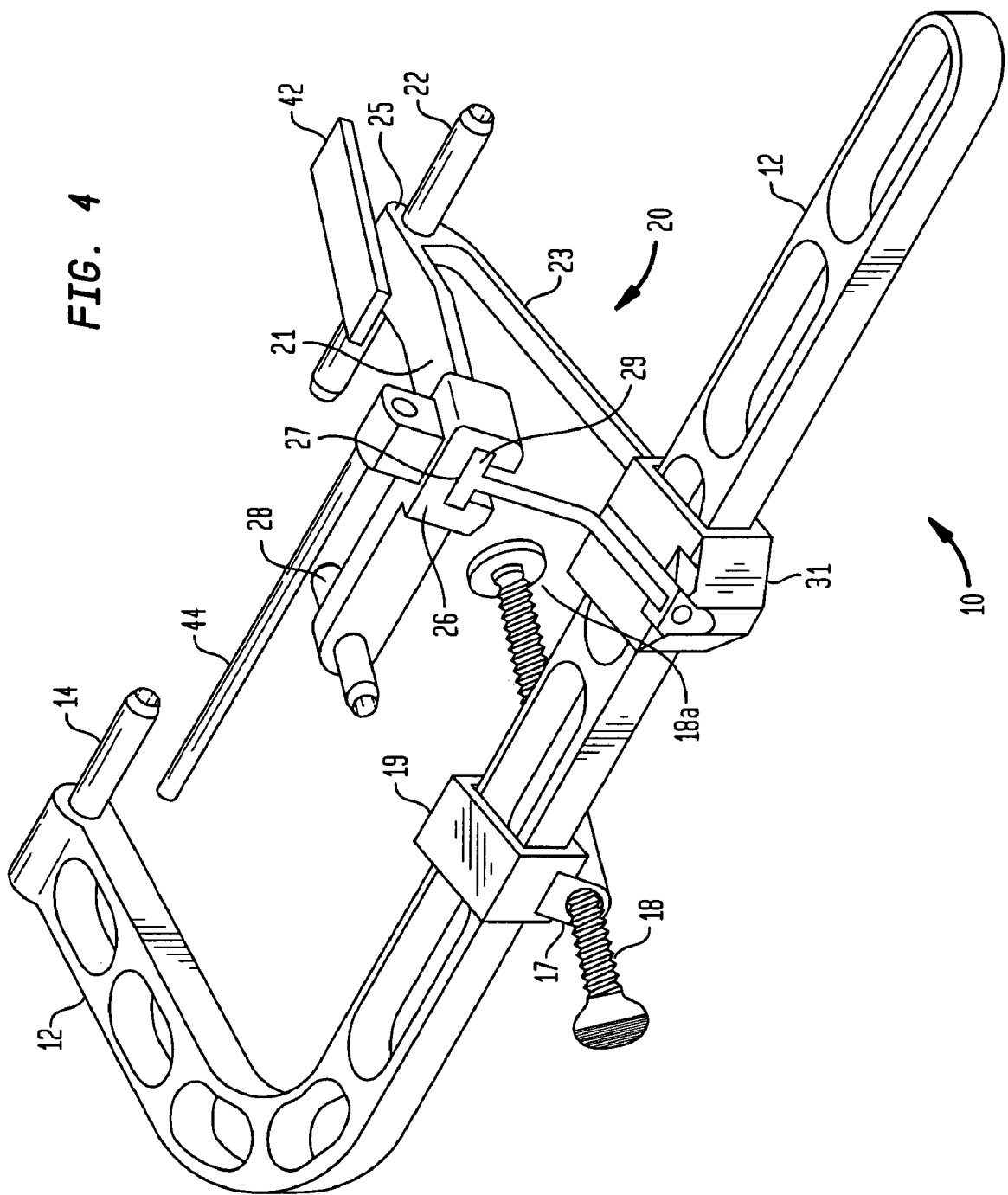
FIG. 4 is an isometric view of the alignment apparatus shown in FIG. 1.

Referring to FIGS. 3 and 4, there is shown a lateral elevation view and an isometric view of the alignment apparatus of FIGS. 1 and 2, including the frame 12, side plate 20, and drill block 26. In particular, the structure of side plate 20 can be seen, including a first arm 21 and a second arm 23 extending from a central portion 25 at divergent angles. The central portion 25 is engaged with the second bushing 22 and is configured to rotate around the longitudinal axis thereof as the frame pivots during positioning of the apparatus. Each arm 21, 23 of slide plate 20 is composed of a rigid material and is rigidly attached to central portion 25. The first arm 21 connects the central portion 25 of side plate 20 with the drill block 26. The second arm 23 connects the central portion 25 of side plate 20 with the frame 12. Thus, as the position of the frame 12 changes, thereby changing the position of second arm 23, the central portion 25 rotates about the axis of the second bushing 22, and the first arm 21 rotates a corresponding distance.

Also shown in FIGS. 3 and 4 is the relationship between adjustment screw 18 and third bushing 28. Adjustment screw 18 is connected to frame 12, as discussed above, at a location medial to side plate 20. Side plate 20 is attached to frame 12 by means of a connecting component 31. Connecting component 31 is configured to engage frame 12 so as to prevent movement between side plate 20 and frame 12 in a vertical as well as anterior-posterior direction, while allowing movement in a lateral direction. Such movement may be limited by a set screw (not shown) or friction fit. Drill block 26 is connected to side plate 20, as discussed above, and third bushing 28 is connected to drill block 26. Accordingly, as adjustment screw 18 is advanced or retracted, thereby changing the anterior-posterior angle of frame 12 with respect to the bone, the angle of third bushing 28 is correspondingly adjusted. In this way, advancement or retraction of adjustment screw 18 may be used to align third bushing 28 with the anatomic anterior-posterior slope of the tibia 40.

Alignment apparatus 10 may be formed of a material that allows for multiple uses, which includes the ability to be repeatedly subjected to the various sterilization procedures used in the art. Acceptable materials for such an embodiment of alignment apparatus 10 include, but are not limited to, surgical stainless steel, titanium, or other similar materials. Alternatively, alignment apparatus 10, or components thereof, may be formed of a material suitable for single use and disposal. Acceptable materials for this embodiment include, but are not limited to, fiber reinforced composites, rigid plastics, or other similar materials.

Figure 5:
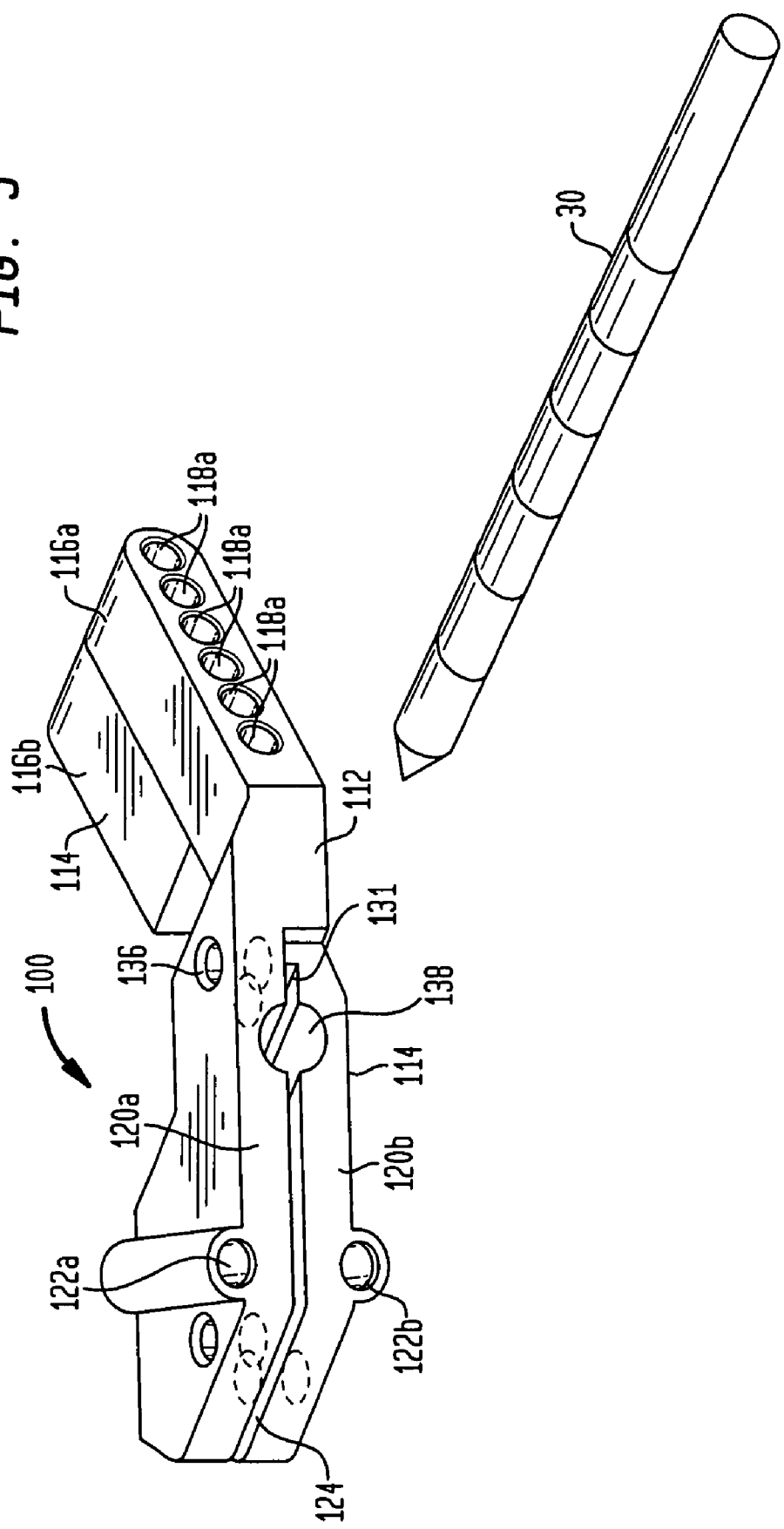
FIG. 5 is an isometric view of a cutting guide according to the present invention.
Figure 6:
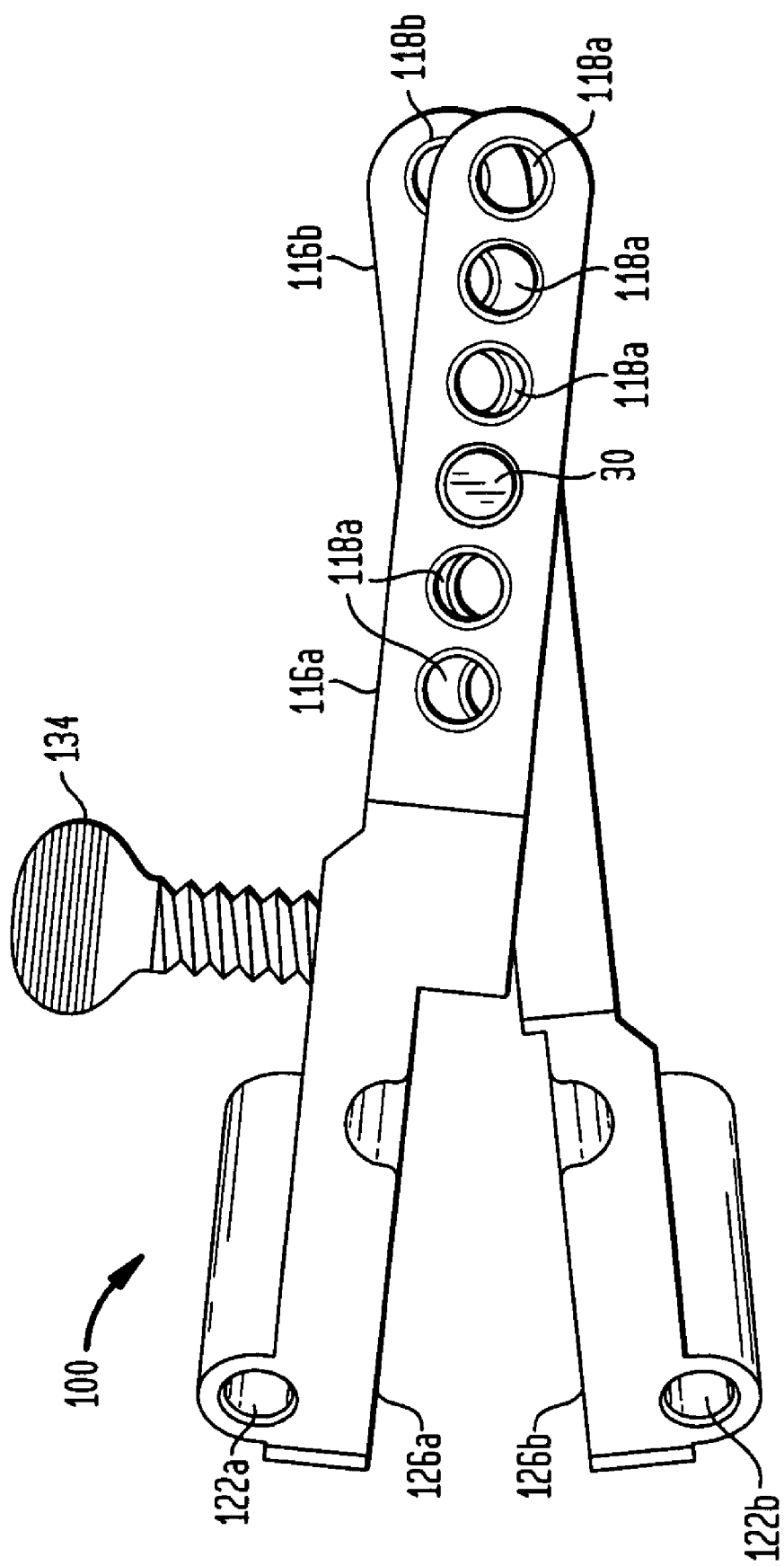
FIG. 6 is an elevation view of the cutting guide of FIG. 5 from an anterior direction.

An exemplary embodiment of a cutting guide 100 according to an embodiment of the present invention is shown in FIG. 5. Generally, cutting guide 100 is adapted to be affixed to a bone surface, and, in the particular embodiment shown in FIG. 5, is adapted to be affixed to the anterior surface of the proximal portion of a human tibia. Cutting guide 100 includes a hinge portion 116 on one end and a guide portion 120a, 120b on another end.

Hinge portion 116 is adapted to be positioned partially over the patellar tendon which is associated with the proximal tibia and to extend toward a first side thereof. Guide portion 120 is adapted to contact a portion of the proximal tibia on a second side of the patellar tendon such that hinge portion 116 is spaced apart from the anterior surface of the proximal tibia at a distance adequate to prevent hinge portion 116 from contacting or otherwise interfering with the patellar tendon. By way of example, guide 100 is shown and described as being adapted for performing what is generally-known as an opening wedge HTO including forming a single cut through the medial cortex of a patient's left proximal tibia. As shown in FIGS. 5 through 8, guide portions 120*a* and 120*b* are preferably shaped so as to extend from the proximal outer surface M of the tibia toward and partially contacting the medial surface of the tibia at N extending substantially toward the posterior cortex of the tibia. Cutting guide slot 124 is preferably included in this portion of cutting guide 100.

Guide 100, preferably, includes two portions: a first arm 112 and a second arm 114. First arm 112 includes a first guide portion 120*a* and a first hinge portion 116*a*, and second arm 114 includes a second guide portion 120*b* and a second hinge portion 116*b*. Hinge portions 116*a*, 116*b* are structured to allow first arm 112 and second arm 114 to rotate with respect to each other. Preferably, this is achieved by including matching holes 118*a*, 118*b* in first and second hinge portions 116*a*, 116*b*, respectively. In the example of cutting guide 100 shown in FIG. 5, first hinge portion 116*a* is positioned anteriorly of second hinge portion 116*b* such that hole 118*a* aligns with hole 118*b* along the respective longitudinal axes thereof. A hinge pin 30 is inserted through a selected hole 118*a*, 118*b*, depending on the anatomy of the particular tibia involved in the procedure, to secure the relative position of first and second arms 112, 114 in the proximal-distal and medial-lateral directions while permitting first arm 112 and second arm 114 to rotate relative to each other. Preferably, hinge pin 30 is also used in affixing guide 100 to the proximal tibia by inserting hinge pin 30 into a hole that is formed, preferably by drilling, in the proximal tibia at the appropriate location as determined by the alignment apparatus 10.

In a preferred embodiment, hinge portions 116*a*, 116*b* each include multiple pairs of holes 118*a*, 118*b*, which allow the user of guide 100 to select the appropriate pair into which to insert hinge pin 30. This allows guide 100 to be adapted to better fit the shape and structure of the specific proximal tibia on which the procedure is carried out, particularly with respect to the location of guide portion 120 and hinge pin 30.

Guide portion 120 includes a cutting guide slot 124 formed therein, which is adapted for use with various forms of cutting instruments used in orthopedic procedures. These cutting instruments include various forms of bone saws, such as oscillating saws, osteotomes and oscillating tip saw blades. Cutting guide slot 124 is formed by a first cutting guide surface 126*a* formed on first guide portion 120*a* and a second cutting guide surface 126*b* formed on second guide portion 120*b*. First and second arms 112, 114 can be rotated into a position such that first and second cutting guide surfaces 126*a*, 126*b* are substantially parallel to each other and are spaced apart from each other at a distance sufficient to accept a cutting instrument therebetween, allowing the cutting instrument to slide freely within cutting guide slot 124 while providing a fit that is sufficient to accurately guide the cutting instrument along a path defined by cutting guide slot 124.

Figure 7:
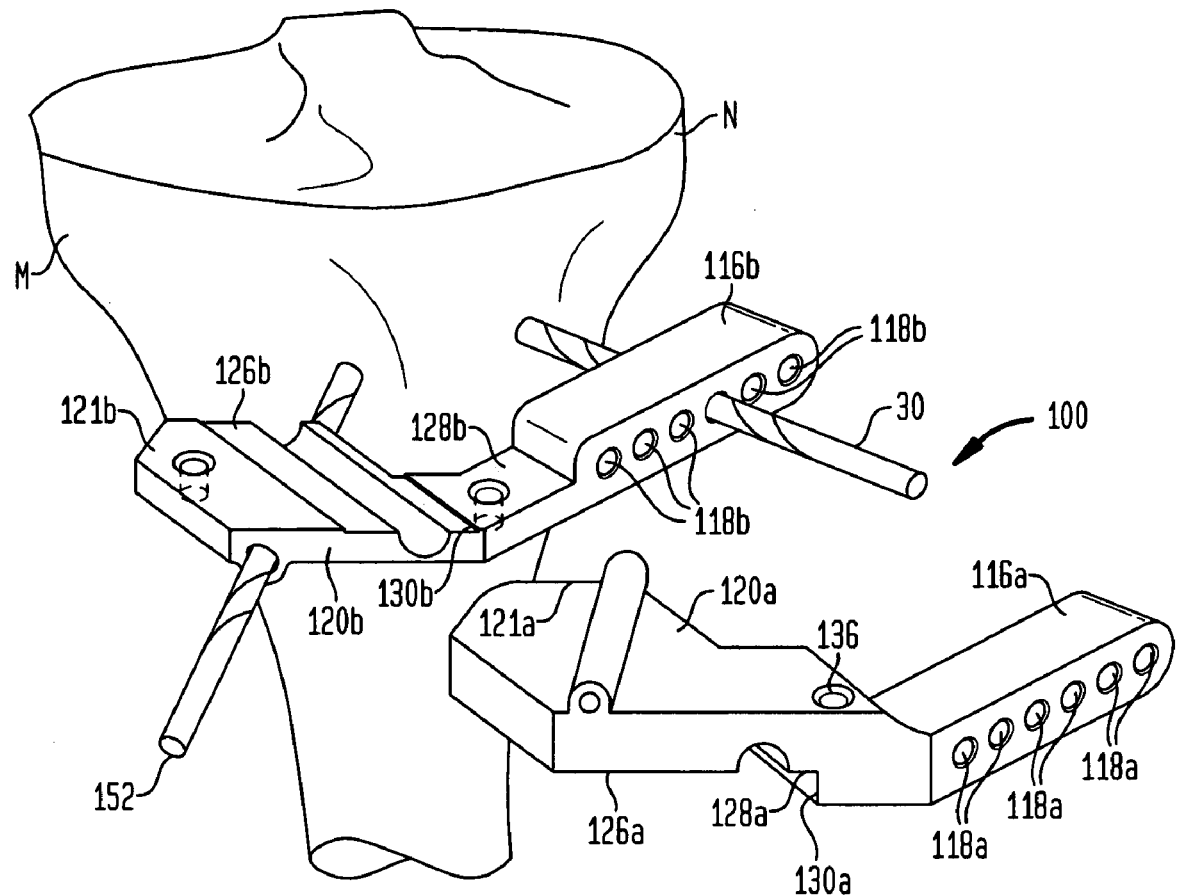
FIG. 7 is an exploded view of a cutting guide affixed to a proximal tibia.
Figure 8:
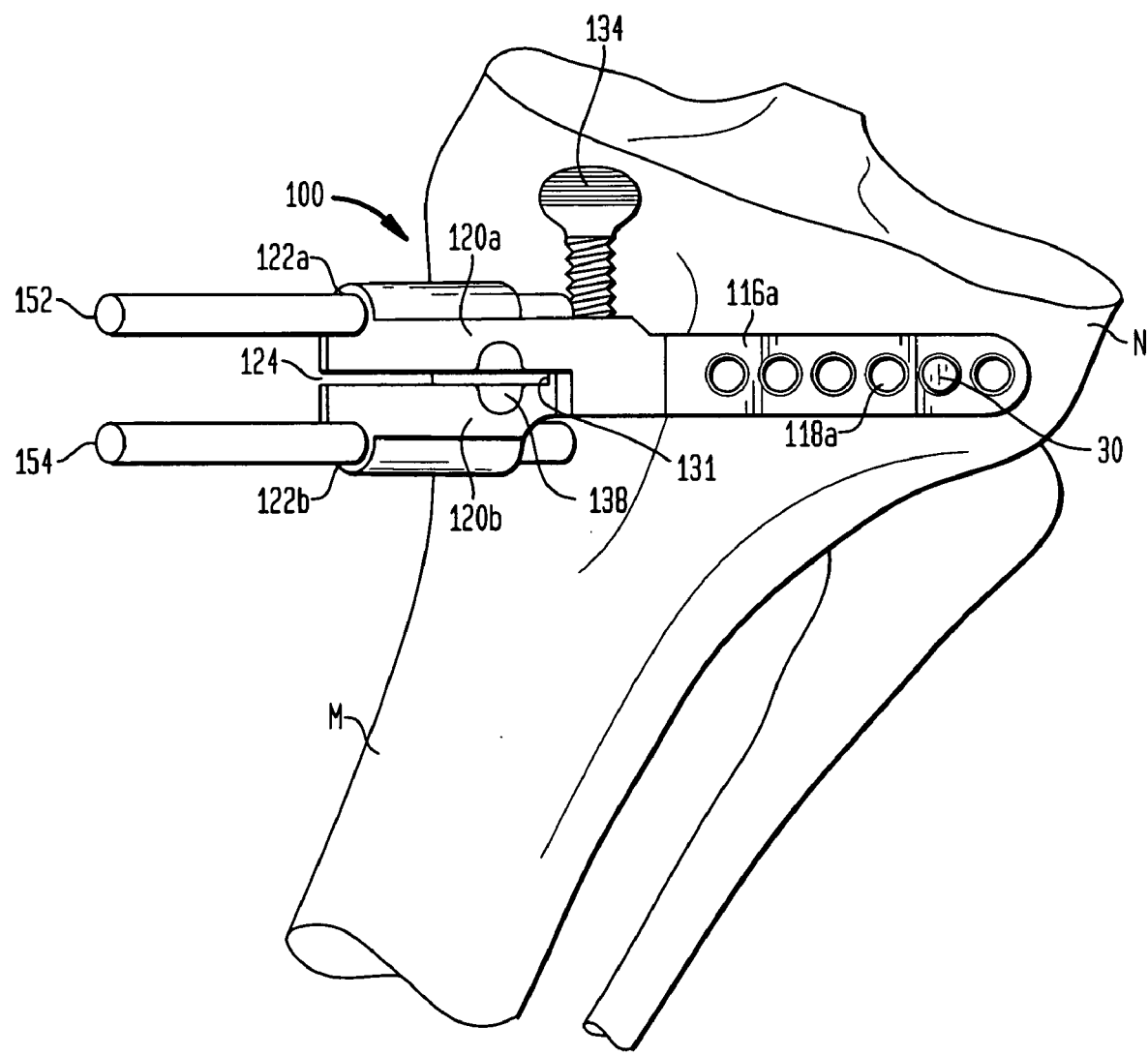
FIG. 8 is an anterior elevation view of the cutting guide shown in FIG. 5 affixed to a proximal tibia.

As shown in FIG. 7, to allow for more accurate spacing between first cutting guide surface 126*a* and second cutting guide surface 126*b* during use and placement of cutting guide 100, first arm 112 and second arm 114 can, respectively, include a first blocking surface 128*a* and a second blocking surface 128*b*. As shown in FIG. 7, blocking surfaces 128*a*, 128*b* are substantially parallel to their respective cutting guide surfaces 126*a*, 126*b* and are spaced apart therefrom. Preferably, blocking surfaces 128*a*, 128*b* are spaced apart from their respective cutting guide surfaces 126*a*, 126*b* at a distance that is approximately equal to half of the desired distance between first and second cutting guide surfaces 126*a*, 126*b*. Alternatively, only one blocking surface may be included on either first arm 112 or second arm 114 at a sufficient height to ensure proper spacing between cutting guide surfaces 126*a*, 126*b*.

First and second arms 112, 114 can further include vertical walls 130*a*, 130*b*, respectively, positioned between the respective cutting guide surfaces 126*a*, 126*b* and blocking surfaces 128*a*, 128*b*. Vertical walls 130*a*, 130*b* act in conjunction with cutting guide surfaces 126*a*, 126*b* to form a terminal end 131 for cutting guide slot 124 that can further act to properly guide a cutting instrument during use with cutting guide 100.

Cutting guide 100 further includes a distraction mechanism formed integrally therewith. The distraction mechanism is used in manipulating the rotational relationship between first arm 112 and second arm 114. In the embodiment shown in FIGS. 5-7, the distraction mechanism includes a threaded hole 136 formed in first arm 112 into which a screw 134 is operatively engaged. When screw 134 is advanced into hole 136, it contacts a portion of second arm 114, such as blocking surface 128*b*, causing a force to be exerted thereon, which acts to cause first arm 112 and second arm 114 to rotate with respect to each other such that first and second cutting guide surfaces 126*a*, 126*b* move away from each other. In an alternative embodiment, the distraction mechanism may include a through hole formed in first arm 112, a threaded hole formed in second arm 114 and a screw. The screw passes through the appropriately-sized through hole and engages the treaded hole. The head of the screw is positioned on the outside surface of first arm 112 such that, when screw 134 is advanced into the threaded hole, the inside surface of the screw head is drawn into contact with the first arm. This contact causes a force to be exerted between first and second arms 112, 114 causing rotational movement therebetween such that first and second cutting guide surfaces 126*a*, 126*b* move toward one another.

Cutting guide 100 is formed of a material sufficient to give cutting guide 100 an appropriate rigidity to accurately guide a cutting instrument for formation of the cuts necessary for the HTO procedure. Additionally, cutting guide 100 may be made from a material that allows for multiple uses, which includes the ability to be repeatedly subjected to the various sterilization procedures used in the art. Acceptable materials for cutting guide 10 include, but are not limited to, surgical stainless steel, titanium, or other similar materials.

A further embodiment of the present invention includes a method for performing an HTO procedure on a patient using alignment apparatus 10, shown in FIGS. 1-4, in conjunction with cutting guide 100, shown in FIGS. 5-8. In performing this procedure, access is gained to the proximal tibia through an appropriately sized, antero-medial incision. The first bushing 14 is placed against the medial cortex 32 of the tibia and the first fixation pin 16 is inserted into the bone approximately one to two centimeters below the knee joint. The longitudinal axis of the first fixation pin 16 may preferably be aligned parallel to the joint line 38 and the coronal plane 36 of the tibia.

Slide plate 20 is then moved relative to the frame 12 in a medial direction until the second bushing 22 contacts the lateral cortex 34 of the tibia through a small incision or "stab" wound. With the second bushing 22 placed against the lateral cortex 34 of the tibia, the second fixation pin 24 is inserted into the bone approximately one to two centimeters below the knee joint. The longitudinal axis of the second fixation pin 24 may preferably be aligned parallel to the joint line 38 and the coronal plane 35 of the tibia. A fixation pin slope indicator 44 may assist in referencing the orientation of the axes of the first and second fixation pins relative to the joint line 38 and the coronal plane 36. Further preferably, the longitudinal axes of the first fixation pin 16 and the second fixation pin 24 may be aligned coaxially.

With the first and second fixation pins inserted into the bone at the correct orientation, the drill block 26 is attached to the side plate 20. The drill block 26, with the third bushing 28 attached thereto is then moved in a posterior direction until the third bushing 28 contacts the anterior-lateral cortex of the tibia through another small incision or "stab" wound. The adjustment screw 18 is advanced until it rests on the anterior tibia and the third bushing 28 is oriented with its longitudinal axis parallel to the anatomic anterior-posterior slope of the tibia 40. A hinge pin slope indicator 42 (shown in FIGS. 3 and 4) may assist in referencing the anatomic anterior-posterior slope of the tibia.

With the third bushing 28 properly aligned, the hinge pin 30 is inserted through the tibia until full penetration of the posterior-lateral cortex of the tibia is achieved. During this step of the procedure, the longitudinal axis of the third bushing 28 is preferably offset a predetermined distance from the tip of the second bushing 24, thus ensuring that a desired minimum lateral cortex thickness remains. With the hinge pin 30 in place, the alignment apparatus 10, including the first and second fixation pins, may be removed from the tibia, leaving the hinge pin 30 in the bone.

With the hinge pin 30 in place in the bone, cutting guide 100 may be assembled. To accomplish this, the second arm 114 of the cutting guide 100 is assembled onto hinge pin 30 by sliding hinge pin 30 through hole 118b or an appropriately-selected one of a set of holes. Generally, one of a set of holes 118b is selected such that guide portion 120 contacts the proximal tibia along the back edge 121a thereof, while providing appropriate anterior spacing of hinge portion 116 relative to the patellar tendon, such that hinge portion 116 does not interfere with the patellar tendon. The proper angular alignment is selected for second arm 114, which is such that second cutting guide surface 126b is aligned with the selected position for the cut to be formed in connection with the procedure. Guide hole 122b is then used as a guide for forming a first drill hole in the proximal tibia. A first pin 154 is then inserted into the first drill hole to secure the position of second arm 114 relative to the proximal tibia.

First arm 112 is then affixed to the proximal tibia by first engaging hole 118a with hinge pin 30 and sliding first arm 112 along hinge pin 30 until the back edge 121a of first arm 112 contacts the proximal tibia. First arm 112 is then aligned such that first blocking surface 128a contacts second blocking surface 128b. A second drill hole is then formed in the proximal tibia using first hole 122a. A second pin 152 is then inserted through hole 122a and into the second drill hole. In a preferred embodiment of guide 100, holes 122a, 122b are formed substantially parallel to each other and are further formed at an angle relative to holes 118a, 118b such that when pins are inserted into guide 100 so as to affix guide 100 to the proximal tibia, the angular arrangement of pins 152, 154 helps to retain guide 100 in its position.

Figure 9:
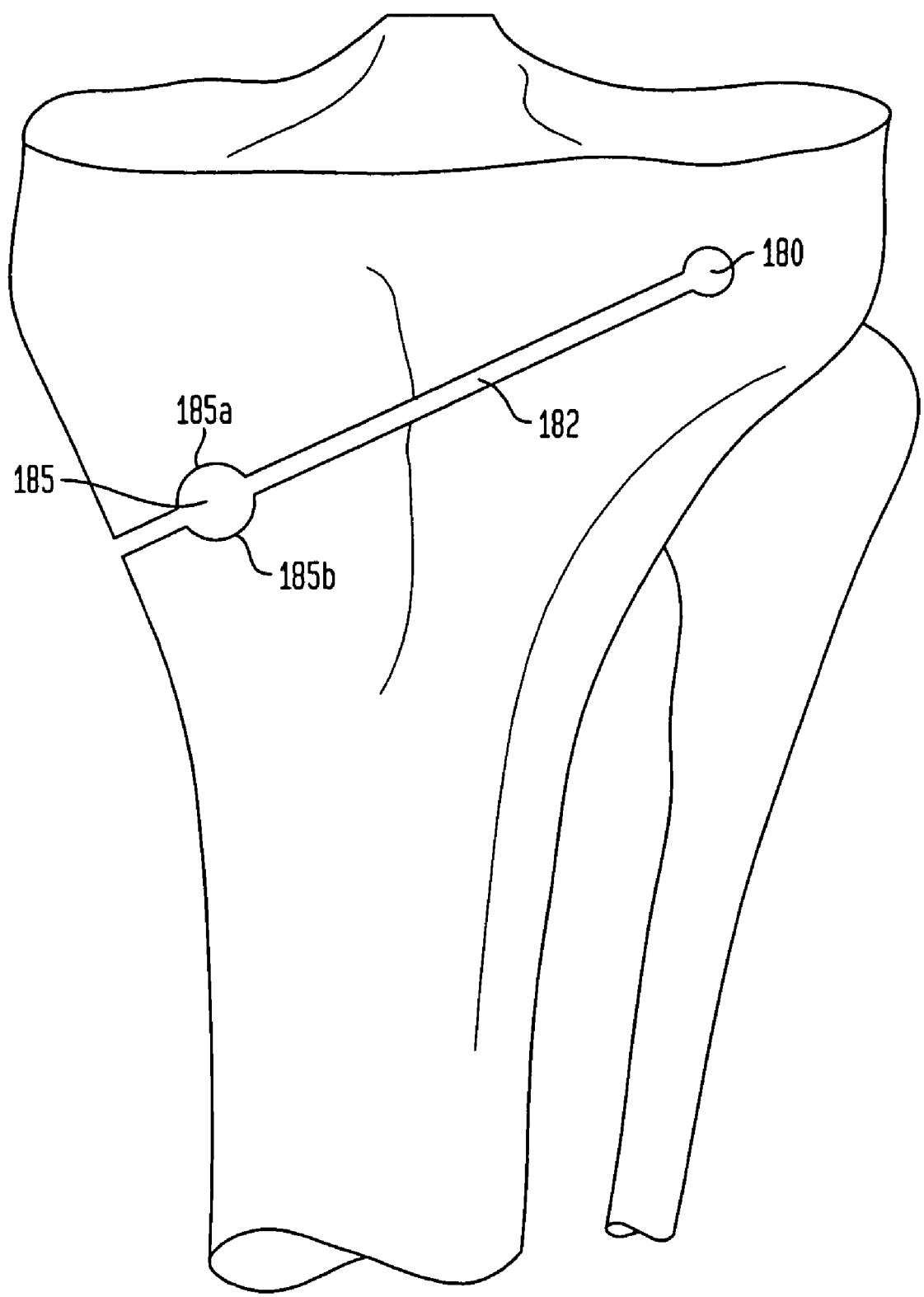
FIG. 9 is an anterior elevation view of a proximal tibia having a cut formed therein using the cutting guide shown in FIG. 5.

Once first and second arms 112, 114 of guide 100 are affixed to the proximal tibia in the proper position, a cutting instrument, as described above, is slid into the cutting guide slot 124, which is formed by first and second cutting guide surfaces 126a, 126b, in order to form an appropriate cut 182 (shown in FIG. 9) in the proximal tibia. Preferably, the cutting instrument is positioned in a generally anterior-posterior direction such that a side edge thereof contacts the terminal end 131 of cutting guide slot 124. Terminal end 131 is preferably of a sufficient length in the anterior-posterior direction to provide stability for the cutting instrument along the plane formed by terminal end 131. Preferably, the cut 182 is initiated by engaging the cutting instrument with cutting guide slot 124 such that an edge of the cutting instrument abuts terminal end 131 so as to be slidably engaged therewith, thereby assisting the user in making cut 182 such that it is oriented substantially in the anterior-posterior direction through the anterior cortex of the tibia without interfering with the patellar tendon. The cutting instrument is then continued to be moved substantially in the anterior-posterior direction until cut 182 penetrates the posterior cortex of the tibia.

Once cut 182 has been started, the user of guide 100 may then proceed to complete cut 182 by freely moving the cutting instrument within cutting guide slot 124. Such movement may include rotating the cutting instrument along the plane formed by cutting guide slot 124 so as to extend cut 182 behind the patellar tendon of the patient and through the entire proximal tibia along the proscribed cutting path. The placement of hinge pin 30 at the hinge portion between first and second arms 112, 114 effectively blocks cutting guide therealong, forming the end of the cut at the desired location and providing a widened, rounded apex of the cut that reduces the stress concentration that may result from subsequent expansion of the cut.

Having completed the formation of cut 182 in the proximal tibia, the user of guide 100 then removes the cutting instrument from cutting guide slot 124 and inserts screw 134 into threaded hole 136. Screw 134 is then turned so as to advance it into threaded hole 136 such that the tip of screw 134 contacts a portion of second arm 114 and creates a force between first arm 112 and second arm 114, which is then transferred, via pins 152, 154 into the proximal tibia at a location above and below cut 182. The continued advancement of screw 134 causes cut 182 to open by forcing apart the portions of proximal tibia that are separated by cut 182. This requires the portion of proximal tibia that is left connecting the two separate portions to flex to accommodate the opening cut 182. The screw is turned, thereby opening cut 182 into the shape of a wedge having the appropriate angle for correction of the defect.

Figure 10:
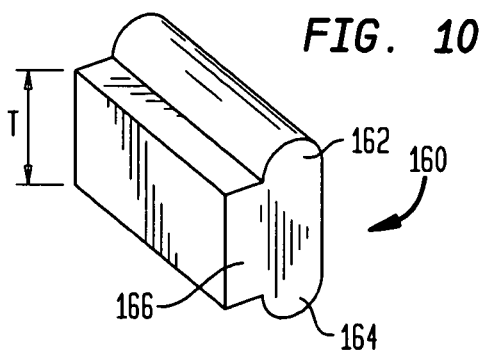
FIG. 10 is an isometric view of an implant used in securing a cut formed during a procedure utilizing a cutting guide according to an embodiment of the present invention.
Figure 11:
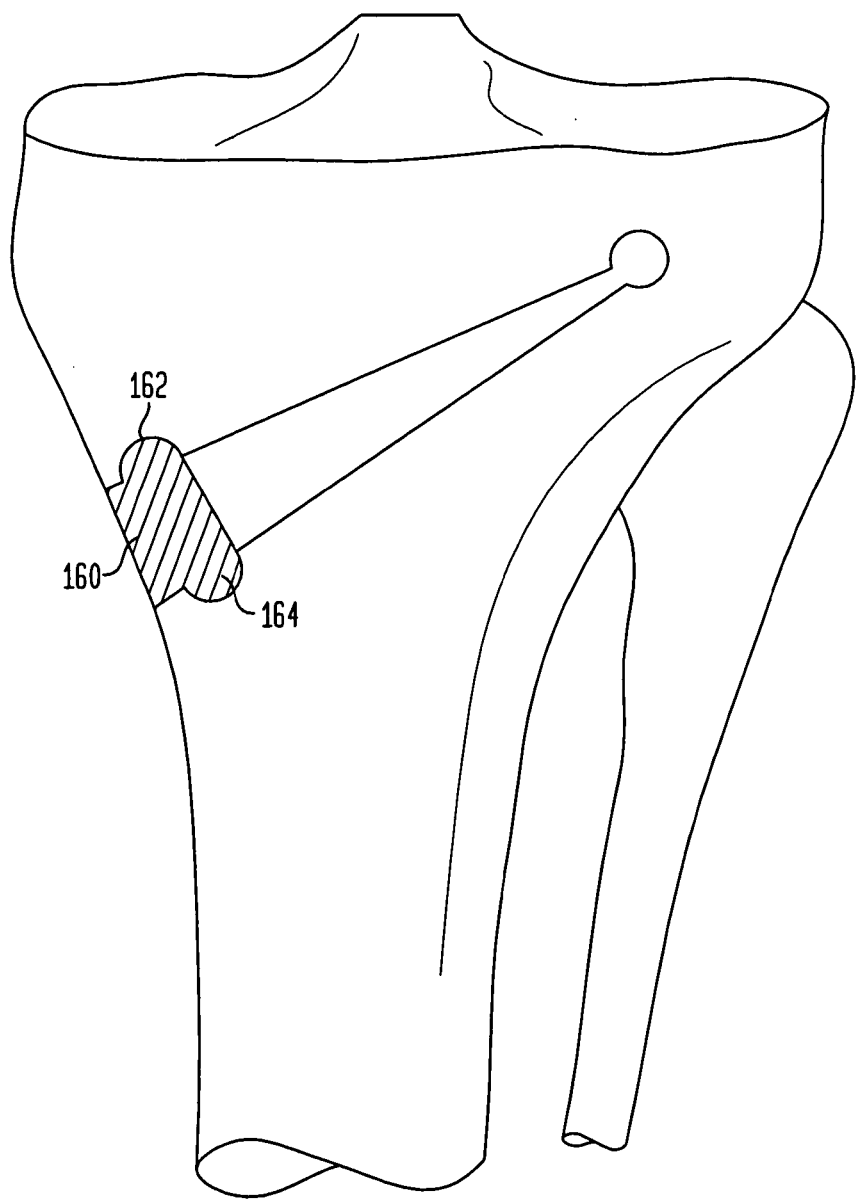
FIG. 11 is an anterior view of a cut formed in a proximal tibia using a cutting guide according to an embodiment of the present invention and secured with the implant shown in FIG. 10.

The bone is then secured in the position achieved through advancement of the screw 134. This can be done by using known devices including staples or spacers. A preferred embodiment of guide 100 includes a drill guide 138 formed between first and second cutting guide surfaces 126a, 126b such that a drill can be guided thereby into the proximal tibia when guide 100 is secured to the proximal tibia in the closed position. The drill used in conjunction with drill guide 138 is sized so that portions of the drill hole form semi-cylindrical channels 185a, 185b on both sides of cut 182. In a procedure using such a drill guide, a drill hole is formed using a drill in conjunction with drill guide 138, preferably prior to forming the cut in the proximal tibial. The wedge can then be secured in position using a spacer 160 shown in FIGS. 10 and 11. The spacer is described in copending U.S. patent application Ser. No. 12/002,002, the disclosure of which is hereby incorporated herein by reference. Spacer 160 includes semi-cylindrical projections 162, 164 extending from opposite sides thereof which are adapted to mate with the corresponding channels 185a, 185b formed in the proximal tibia and a flange 166 that extends between the inner surfaces of the wedge. The thickness T of flange 166 is selected to maintain the appropriate angle for the wedge formed during the procedure. Flange 166 may be angled so as to substantially match the desired angle for the wedge.

The mating of projections 162, 164 with channels 185*a*, 185*b* helps to provide stability for the spacer and the joint overall during the healing process. In particular, it helps to add to the torsional stability of the tibial plateau relative to the remainder of the bone to aid in insertion of spacer 160. Screw 134 may be turned so as to expand the size of the wedge beyond the desired angle for correction of the defect. Once spacer 160 is in place, the cutting guide 100 and hinge pin 30 are then removed from the bone, and the wound is closed.

Although the invention herein has been described with reference to particular embodiments, it is to be understood that these embodiments are merely illustrative of the principles and applications of the present invention. For example, the alignment apparatus 10 has been described herein in conjunction with a cutting guide 100 used to perform opening-wedge HTO procedures. However, the alignment apparatus 10 may also be used in conjunction with cutting guides used to perform other types of procedures, such as closing-wedge HTO procedures. It is therefore to be understood that numerous modifications may be made to the illustrative embodiments and that other arrangements may be devised without departing from the spirit and scope of the present invention as defined by the appended claims.

The invention claimed is:

1. An apparatus to aid in cutting a bone during a bone osteotomy procedure comprising:
    a frame connected to a first bushing adapted to receive a first fixation pin along a first axis;
    a side plate attached to the frame and moveable with respect thereto, the side plate connected to a second bushing adapted to receive a second fixation pin along the first axis;
    a drill block attached to the side plate, the drill block having connected to a third bushing adapted to receive a hinge pin along a second axis transverse to the first axis; and
    an adjustment mechanism connected to the frame and extending transverse to the first axis, the adjustment mechanism being adapted to contact the bone when the apparatus is positioned with respect to the bone during the bone osteotomy procedure with the first and second fixation pins being secured to opposite sides of the bone, wherein actuation of the adjustment mechanism causes the adjustment mechanism to apply a force between the bone and the frame so as to rotate the third bushing about the first axis.

2. The apparatus of claim 1, wherein
the adjustment mechanism is an adjustment screw.

3. The apparatus of claim 2, wherein the adjustment screw is configured to contact an anterior tibia and adjust the angle of the frame with respect to the anatomic anterior-posterior slope of the tibia.

4. The apparatus of claim 1, wherein the hinge pin is configured to fully penetrate the posterior-lateral cortex of a tibia.

5. The apparatus of claim 1, wherein the longitudinal axis of the third bushing is offset a predetermined distance medially from the tip of the second bushing, thereby ensuring that a desired minimum lateral cortex bone thickness remains.

6. The apparatus of claim 1, wherein the drill block is releasably attached to the side plate.

7. The apparatus of claim 1, wherein the drill block is movable with respect to the side plate.

8. The apparatus of claim 7, wherein the drill block is movable with respect to the side plate along the second axis.

9. The apparatus of claim 1, wherein the side plate is movable with respect to the frame along the first axis.

10. A method of cutting a bone during a bone osteotomy procedure comprising:
    providing an alignment device having a first bone referencing portion, a second bone referencing portion, and a third bone referencing portion, the third bone referencing portion having a hinge pin guide;
    securing the first bone referencing portion to a medial cortex of a tibia;
    securing the second bone referencing portion to a lateral cortex of the tibia;
    positioning the third bone referencing portion adjacent the anterior-lateral cortex of the tibia with the hinge pin guide parallel to an anatomic anterior-posterior slope of the tibia by rotating the device about the first and second referencing portions;
    inserting a hinge pin into the tibia through the hinge pin guide;
    attaching a cutting guide to the hinge pin; and
    forming a cut using a cutting instrument in connection with the cutting guide.

11. The method of claim 10, wherein the alignment device includes a frame and the first bone referencing portion includes a first bushing engaged with the frame.

12. The method of claim 11, further comprising providing a lateral side plate configured to engage with the frame and a second bushing engaged with the side plate and forming a part of the second bone referencing portion.

13. The method of claim 12, further comprising offsetting the longitudinal axis of the hinge pin guide a predetermined distance from the tip of the second bushing, thereby ensuring that a desired minimum lateral cortex bone thickness remains.

14. The method of claim 12, further comprising providing a second fixation pin forming a part of the second bone referencing portion and configured to secure the second bone referencing portion to the tibia at a position between about 1 to 2 cm below a knee joint.

15. The method of claim 14, further comprising orienting the second fixation pin parallel to the joint line and the coronal plane of the tibia.

16. The method of claim 10, further comprising providing a first fixation pin forming a part of the first bone referencing portion and configured to secure the first bone referencing portion to the tibia at a position between about 1 to 2 cm below a knee joint.

17. The method of claim 16, further comprising orienting the first fixation pin parallel to the joint line and the coronal plane of the tibia.

18. The method of claim 11, further comprising providing an adjustment screw attached to the frame, the adjustment screw configured to contact the anterior tibia and determining the orientation of the frame with respect to the anatomic anterior-posterior slope of the tibia.

19. A method of cutting a bone during a bone osteotomy procedure comprising:
    providing an alignment device having a frame, side plate, and a drill block; the frame having an adjustment screw and being configured to receive a first bushing, the side plate being moveable with respect to the frame and configured to receive a second bushing, and the drill block being releasably attached and moveable with respect to the side plate and configured to receive a third bushing;
    placing the first bushing against the medial cortex of a tibia;
    inserting a first pin through the first bushing and into the tibia;

moving the side plate along the frame in a medial direction and attaching the second bushing thereto such that the second bushing contacts the lateral cortex of the tibia;

inserting a second pin through the second bushing and into the tibia;

attaching the drill block to the side plate, moving the drill block in a posterior direction, and attaching the third bushing such that the third bushing contacts the anterior-lateral cortex of the tibia;

advancing the adjustment screw until it contacts the anterior tibia and the drill block is oriented parallel to the anatomic anterior-posterior slope of the tibia;

inserting a hinge pin through the third bushing and into the anterior-lateral cortex of the tibia;

attaching a cutting guide to the hinge pin; and forming a cut through a portion of the tibia using a cutting instrument in connection with cutting guide surfaces of the cutting guide.

20. The method of claim 19, further comprising inserting the first pin into the tibia at a location about 1 to 2 cm below a joint line.

21. The method of claim 19, further comprising inserting the second pin into the tibia at a location about 1 to 2 cm below a joint line.

22. The method of claim 19, further comprising coaxially aligning the first and second pins parallel to a joint line and a coronal plane of the tibia.

23. The method of claim 19, further comprising offsetting the longitudinal axis of the third bushing a predetermined distance medially from the tip of the second bushing, thereby ensuring that a desired minimum lateral cortex bone thickness remains.

* * * * *

UNITED STATES PATENT AND TRADEMARK OFFICE
CERTIFICATE OF CORRECTION

| | |
|---|---|
| PATENT NO. | : 8,192,441 B2 |
| APPLICATION NO. | : 12/287061 |
| DATED | : June 5, 2012 |
| INVENTOR(S) | : Carlos E. Collazo |

Page 1 of 1

It is certified that error appears in the above-identified patent and that said Letters Patent is hereby corrected as shown below:

In the Claims
Column 11, line 34, Claim 1, after "block" delete "having" second occurrence
Column 12, line 57, Claim 19, after "frame," insert --a--

Signed and Sealed this
Thirtieth Day of September, 2014

Michelle K. Lee
*Deputy Director of the United States Patent and Trademark Office*